(12) United States Patent
Ediger et al.

(10) Patent No.: US 7,725,144 B2
(45) Date of Patent: May 25, 2010

(54) DETERMINATION OF DISEASE STATE USING RAMAN SPECTROSCOPY OF TISSUE

(75) Inventors: Marwood Neal Ediger, Albuquerque, NM (US); Craig M. Gardner, Arlington, MA (US); Edward L. Hull, Fairport, NY (US)

(73) Assignee: VeraLight, Inc., Albuquerque, NM (US)

(*) Notice: Subject to any disclaimer, the term of this patent is extended or adjusted under 35 U.S.C. 154(b) by 1243 days.

(21) Appl. No.: 10/742,110

(22) Filed: Dec. 19, 2003

(65) Prior Publication Data

US 2005/0090750 A1    Apr. 28, 2005

Related U.S. Application Data

(63) Continuation-in-part of application No. 10/116,272, filed on Apr. 4, 2002, now Pat. No. 7,043,288.

(60) Provisional application No. 60/515,343, filed on Oct. 28, 2003, provisional application No. 60/517,418, filed on Nov. 4, 2003.

(51) Int. Cl.
*A61B 5/00* (2006.01)

(52) U.S. Cl. .................... 600/310; 600/342; 600/476; 600/478; 600/407; 398/79; 356/301

(58) Field of Classification Search ............... 600/476, 600/477, 473, 310, 475, 431, 342; 424/9.1; 398/79; 356/301
See application file for complete search history.

(56) References Cited

U.S. PATENT DOCUMENTS

| | | | | |
|---|---|---|---|---|
| 5,313,941 | A | 5/1994 | Braig et al. | 128/633 |
| 5,348,003 | A | 9/1994 | Caro | 128/633 |
| 5,553,616 | A * | 9/1996 | Ham et al. | 600/316 |
| 5,582,168 | A | 12/1996 | Samuels et al. | 128/633 |
| 5,612,540 | A | 3/1997 | Richards-Kortum et al. | 250/461.2 |
| 5,615,673 | A * | 4/1997 | Berger et al. | 600/326 |
| 5,652,653 | A | 7/1997 | Alsmeyer et al. | 356/301 |

(Continued)

*Primary Examiner*—Brian Casler
*Assistant Examiner*—Joel M Lamprecht
(74) *Attorney, Agent, or Firm*—V. Gerald Grafe

(57) ABSTRACT

A method of determining disease state in an individual. A portion of the tissue of the individual is illuminated with excitation light, then light emitted by the tissue due to Raman scattering of a chemical with the tissue responsive to the excitation light is detected. The detected light can be combined with a model relating Raman emission with disease state to determine a disease state of the individual. The invention can comprise single wavelength excitation light, scanning of excitation light (illuminating the tissue at a plurality of wavelengths), detection at a single wavelength, scanning of detection wavelengths (detecting emitted light at a plurality of wavelengths), and combinations thereof. The invention also can comprise correction techniques that reduce determination errors due to detection of light other than that from Raman emission of a chemical in the tissue. For example, the reflectance of the tissue can lead to errors if appropriate correction is not employed. The invention can also comprise a variety of models relating Raman emission to disease state, including a variety of methods for generating such models. Other biologic information can be used in combination with the Raman spectral properties to aid in the determination of disease state. The invention also comprises apparatuses suitable for carrying out the method, including appropriate light sources, detectors, and models (for example, implemented on computers) used to relate detected Raman emission and disease state.

40 Claims, 7 Drawing Sheets

U.S. PATENT DOCUMENTS

| | | | | |
|---|---|---|---|---|
| 5,784,162 A | | 7/1998 | Cabib et al. | 356/346 |
| 5,845,639 A | * | 12/1998 | Hochman et al. | 600/407 |
| 5,855,882 A | | 1/1999 | Li et al. | 424/94.61 |
| 5,861,238 A | | 1/1999 | Li et al. | 435/2 |
| 5,864,397 A | | 1/1999 | VoDinh | 356/301 |
| 5,882,301 A | | 3/1999 | Yoshida | 600/318 |
| 5,885,224 A | | 3/1999 | Yoshida | 600/558 |
| 5,962,245 A | * | 10/1999 | Li et al. | 435/18 |
| 6,044,285 A | | 3/2000 | Chaiken et al. | 600/316 |
| 6,167,290 A | | 12/2000 | Yang et al. | 600/322 |
| 6,289,230 B1 | | 9/2001 | Chaiken et al. | 600/322 |
| 6,352,502 B1 | | 3/2002 | Chaiken et al. | 600/4.73 |
| 6,353,226 B1 | | 3/2002 | Khalil et al. | 250/341.8 |
| 6,377,828 B1 | | 4/2002 | Chaiken et al. | 600/316 |
| 6,411,838 B1 | * | 6/2002 | Nordstrom et al. | 600/476 |
| 6,485,703 B1 | | 11/2002 | Cote et al. | 424/9.1 |
| 6,505,059 B1 | | 1/2003 | Kollias et al. | 600/316 |
| 6,522,903 B1 | | 2/2003 | Berman et al. | 600/316 |
| 6,560,478 B1 | | 5/2003 | Alfano et al. | 600/473 |
| 6,571,117 B1 | * | 5/2003 | Marbach | 600/473 |
| 6,574,490 B2 | | 6/2003 | Abbink et al. | 600/316 |
| 6,574,501 B2 | | 6/2003 | Lambert et al. | 600/473 |
| 6,609,015 B2 | * | 8/2003 | Lucassen et al. | 600/322 |
| 6,615,061 B1 | | 9/2003 | Khalil et al. | 600/310 |
| 6,630,673 B2 | | 10/2003 | Khalil et al. | 250/341.8 |
| 6,662,030 B2 | * | 12/2003 | Khalil et al. | 600/316 |
| 6,665,556 B1 | * | 12/2003 | Alfano et al. | 600/473 |
| 6,721,583 B1 | * | 4/2004 | Durkin et al. | 600/318 |
| 6,760,613 B2 | * | 7/2004 | Nordstrom et al. | 600/476 |
| 6,853,854 B1 | * | 2/2005 | Proniewicz et al. | 600/319 |
| 6,889,075 B2 | * | 5/2005 | Marchitto et al. | 600/473 |
| 7,113,814 B2 | * | 9/2006 | Ward et al. | 600/310 |
| 2002/0091324 A1 | * | 7/2002 | Kollias et al. | 600/476 |
| 2004/0019283 A1 | * | 1/2004 | Lambert et al. | 600/476 |
| 2004/0092590 A1 | * | 5/2004 | Arterburn et al. | 514/560 |

* cited by examiner

DETERMINATION OF DISEASE STATE USING RAMAN SPECTROSCOPY OF TISSUE

CROSS REFERENCES TO CO-PENDING APPLICATIONS

This application claims priority under 35 U.S.C §120 as a continuation in part of U.S. patent application Ser. No. 10/116,272, entitled "Apparatus And Method For Spectroscopic Analysis Of Tissue To Detect Diabetes In An Individual," filed Apr. 4, 2002, now U.S. Pat. No. 7,043,288, issued May 9, 2006, incorporated herein by reference. This application claims priority under 35 U.S.C §119 to U.S. provisional application 60/515,343, Determination of a Measure of a Glycation End-Product or Disease State Using Tissue Fluorescence," filed Oct. 28, 2003, and U.S. provisional application 60/517,418, filed Nov. 4, 2003 Apparatus and Method for Spectroscopic Analysis of Tissue to Determine Glycation End-products incorporated herein by reference.

FIELD OF THE INVENTION

The present invention generally relates to determination of disease state from Raman spectroscopy in tissue. More specifically, the present invention relates to methods and apparatuses for determining models that relate Raman spectra of tissue to disease state, and for determining properties of Raman spectra in tissue, and for determination of disease state from Raman spectral properties and from appropriate models.

BACKGROUND OF THE INVENTION

Diabetes mellitus is a major health problem in the United States and throughout the world's developed and developing nations. In 2002, the American Diabetes Association (ADA) estimated that 18.2 million Americans—fully 6.4% of the citizenry—were afflicted with some form of diabetes. Of these, 90-95% suffered from type 2 diabetes, and 35%, or about 6 million individuals, were undiagnosed. See ADA Report, *Diabetes Care*, 2003. The World Health Organization (WHO) estimates that 150 million people worldwide suffer from diabetes; type 2 diabetes also represents 90% of all diagnoses worldwide. Unfortunately, projections indicate that this grim situation will worsen in the next two decades. The WHO forecasts that the total number of diabetics will double before the year 2025. Similarly, the ADA estimates that by 2020, 8.0% of the US population, some 20 million individuals, will have contracted the disease. Assuming rates of detection remain static, this portends that, in less than twenty years, three of every 100 Americans will be 'silent' diabetics. It is no surprise that many have characterized the worldwide outbreak of diabetes as epidemic.

Diabetes has a significant impact on individual health and the national economy. U.S. health care costs related to diabetes exceeded $132 billion in 2002. Due to the numerous complications that result from chronic hyperglycemia, these costs were distributed over a wide array of health services. For example, between 5 and 10 percent of all U.S. expenditures in the areas of cardiovascular disease, kidney disease, endocrine and metabolic complications, and ophthalmic disorders were attributable to diabetes. See ADA Report, *Diabetes Care*, 2003. These economic and health burdens belie the fact that most diabetes-related complications are preventable. The landmark Diabetes Control and Complications Trial (DCCT) established that a strict regimen of glucose monitoring, exercise, proper diet, and insulin Research Group, *N Eng J Med*, 1993. Furthermore, the ongoing Diabetes Prevention Program (DPP) has already demonstrated that individuals at risk for diabetes can significantly reduce their chances of contracting the disease by implementing lifestyle changes such a weight loss and increased physical activity. See DPP Research Group, *N Eng J Med*, 2002. ADA has recommended that health care providers begin screening of individuals with one or more disease risk factors, observing: "If the DPP demonstrates a reduction in the incidence of type 2 diabetes as a result of one or more of the [tested] interventions, then more widespread screening . . . may be justified". See ADA Position Statement, *Diabetes Care*, 2003.

The Fasting Plasma Glucose (FPG) test is one of two accepted clinical standards for the diagnosis of or screening for diabetes. See ADA Committee Report, *Diabetes Care*, 2003. The FPG test is a carbohydrate metabolism test that measures plasma glucose levels after a 12-14 hour fast. Fasting stimulates the release of the hormone glucagon, which in turn raises plasma glucose levels. In non-diabetic individuals, the body will produce and process insulin to counteract the rise in glucose levels. In diabetic individuals, plasma glucose levels remain elevated. The ADA recommends that the FPG test be administered in the morning because afternoon tests tend to produce lower readings. In most healthy individuals, FPG levels will fall between 70 and 100 mg/dl. Medications, exercise, and recent illnesses can impact the results of this test, so an appropriate medical history should be taken before it is performed. FPG levels of 126 mg/dl or higher indicate a need for a subsequent retest. If the same levels are reached during the retest, a diagnosis of diabetes mellitus is typically rendered. Results that measure only slightly above the normal range may require further testing, including the Oral Glucose Tolerance Test (OGTT) or a postprandial plasma glucose test, to confirm a diabetes diagnosis. Other conditions that can cause an elevated result include pancreatitis, Cushing's syndrome, liver or kidney disease, eclampsia, and other acute illnesses such as sepsis or myocardial infarction.

Because it is easier to perform and more convenient for patients, the FPG test is strongly recommended by the ADA and is in more widespread use than the other accepted diagnostic standard, the OGTT. The OGTT is the clinical gold standard for diagnosis of diabetes despite various drawbacks. After presenting in a fasting state, the patient is administered an oral dose of glucose solution (75 to 100 grams of dextrose) which typically causes blood glucose levels to rise in the first hour and return to baseline within three hours as the body produces insulin to normalize glucose levels. Blood glucose levels may be measured four to five times over a 3-hour OGTT administration. On average, levels typically peak at 160-180 mg/dl from 30 minutes to 1 hour after administration of the oral glucose dose, and then return to fasting levels of 140 mg/dl or less within two to three hours. Factors such as age, weight, and race can influence results, as can recent illnesses and certain medications. For example, older individuals will have an upper limit increase of 1 mg/dl in glucose tolerance for every year over age 50. Current ADA guidelines dictate a diagnosis of diabetes if the two-hour post-load blood glucose value is greater than 200 mg/dl on two separate OGTTs administered on different days.

In addition to these diagnostic criteria, the ADA also recognizes two 'pre-diabetic' conditions reflecting deviations from euglycemia that, while abnormal, are considered insufficient to merit a diagnosis of diabetes mellitus. An individual is said to have 'Impaired Fasting Glucose' (IFG) when a single FPG test falls between 110 and 126 mg/dl. Similarly, when the OGTT yields 2-hour post-load glucose values between 140 and 200 mg/dl, a diagnosis of 'Impaired Glucose Tolerance' (IGT) is typically rendered. Both of these conditions are considered risk factors for diabetes, and IFG/IGT were used as entrance criteria in the Diabetes Prevention Program. IFG/IGT are also associated with increased risk of cardiovascular disease.

The need for pre-test fasting, invasive blood draws, and repeat testing on multiple days combine to make the OGTT and FPG tests inconvenient for the patient and expensive to administer. In addition, the diagnostic accuracy of these tests leaves significant room for improvement. See, e.g., M. P. Stern, et al., Ann Intern Med, 2002, and J. S. Yudkin et al., BMJ, 1990. Various attempts have been made in the past to avoid the disadvantages of the FPG and OGTT in diabetes screening. For example, risk assessments based on patient history and paper-and-pencil tests have been attempted, but such techniques have typically resulted in lackluster diagnostic accuracy. In addition, the use of glycated hemoglobin (HbA1c) has been suggested for diabetes screening. However, because HbA1c is an indicator of average glycemia over a period of several weeks, its inherent variability combines with the experimental uncertainty associated with currently-available HbA1c assays to make it a rather poor indicator of diabetes. See ADA Committee Report, Diabetes Care, 2003. HbA1c levels of diabetics can overlap those of nondiabetics, making HbA1c problematic as a screening test. A reliable, convenient, and cost-effective means to screen for diabetes mellitus is needed. Also, a reliable, convenient, and cost-effective means for measuring effects of diabetes could help in treating the disease and avoiding complications from the disease.

U.S. Pat. No. 5,553,616 (Ham) discloses instruments and methods for noninvasive tissue glucose level monitoring via Raman spectroscopy and spectral processing by neural networks and fuzzy logic. Ham does not describe measurement of any other tissue property, or any method of screening for or monitoring diabetes.

U.S. Pat. No. 5,582,168 (Samuels) discloses apparatus and methods for measuring characteristics of biological tissues and similar materials. These apparatus and methods are described with respect to measurements of the human eye. In addition, the correction methodologies described by these inventors involve only measurements of the elastically scattered excitation light. Samuels describes a simple linear correction technique. Samuels does not disclose noninvasive measurements that allow determination of tissue disease status.

U.S. Pat. No. 5,882,301 (Yoshida) discloses methods and apparatus for obtaining Raman emission from intraocular substances including advanced glycated endproducts (AGEs). Yoshida does not describe a technique for assessing AGEs in skin or for quantifying the AGE concentration as a means to determine disease status.

U.S. Pat. No. 6,044,285 (Chaiken) discloses a system based upon Raman spectroscopy for measuring blood glucose. The described technique relies upon an absorbing species such as hemoglobin acting as a temperature probe. Chaiken does not disclose measurement of advanced glycation endproducts or other analytes relating to disease status. In addition, Chaiken does not describe methods for correction techniques to compensate for local skin absorption or scattering.

U.S. Pat. No. 6,167,290 (Yang) discloses a Raman spectroscopy system for noninvasively measuring blood glucose. Yang does not disclose measurement of advanced glycation endproducts or other analytes relating to screening for or monitoring diabetes status. Furthermore, Yang does not describe methods for correction techniques to compensate for local skin absorption or scattering in order to recover the intrinsic Raman emission signal.

U.S. Pat. No. 6,289,230 (Chaiken) describes an apparatus for the non-invasive quantification of glucose via Raman spectroscopy. Chaiken does not disclose measurement of advanced glycation endproducts or other analytes relating to disease status. In addition, Chaiken does not describe methods for correction techniques to compensate for local skin absorption or scattering.

U.S. Pat. No. 6,352,502 (Chaiken) describes an apparatus based upon Raman spectroscopy for the noninvasive characterization of skin and detection of skin abnormalities. Chaiken does not disclose measurement of advanced glycation endproducts or other analytes relating to diabetes status. Chaiken does not describe methods to extract the intrinsic Raman emission from the detected signal nor multivariate techniques to quantitatively predict analyte concentration.

U.S. Pat. No. 6,560,478 (Alfano) describes an apparatus based upon Raman spectroscopy for examining biological materials. Alfano discloses that the technique can be applied for the diagnosis of disease by measuring characteristic Raman emission associated with blood glucose and other constituents. Alfano does not describe a method or technique for quantifying Advanced Glycation Endproducts as a metric for assess diabetes status. Also, Alfano does not disclose algorithms or methods for recovering intrinsic Raman emission or other techniques to compensate for local tissue variations.

SUMMARY OF THE INVENTION

The present invention provides a method of determining disease state in an individual. A portion of the tissue of the individual is illuminated with excitation light, then light returned by the tissue due to inelastic Raman scattering by chemicals within the tissue responsive to the excitation light is detected. The detected light can be combined with a model relating Raman spectra with disease state to determine a disease state of the individual. The invention can comprise single wavelength excitation light, scanning of excitation light (illuminating the tissue at a plurality of wavelengths), detection at a single wavelength, scanning of detection wavelengths (detecting emitted light at a plurality of wavelengths), and combinations thereof. The invention also can comprise correction techniques that reduce determination errors due to detection of light other than that from Raman scattering of a chemical in the tissue. For example, the reflectance of the tissue can lead to errors if appropriate correction is not employed. The invention can also comprise a variety of models relating Raman spectra to disease state, including a variety of methods for generating such models. Other biologic information can be used in combination with the Raman spectral properties to aid in the determination of disease state, for example age of the individual, height of the individual, weight of the individual, history of disease in the individual's family, ethnicity, skin melanin content, or a combination thereof. Fluorescence or near-infrared spectroscopic examination can also be used to supply additional information, for example like that discussed in U.S. patent application Ser. No. 10/116,272, entitled "Apparatus And Method For Spectroscopic Analysis Of Tissue To Detect Diabetes In An Individual," filed Apr. 4, 2002. The invention also comprises apparatuses suitable for carrying out the method, including appropriate light sources, detectors, and models (for example, implemented on computers) used to relate detected Raman scattering and disease state.

As used herein, "determining a disease state" includes determining the presence or likelihood of diabetes; the degree of progression of diabetes; a change in the presence, likelihood, or progression of diabetes; a probability of having, not having, developing, or not developing diabetes; the presence, absence, progression, or likelihood of complications from diabetes. "Diabetes" includes a number of blood glucose regulation conditions, including Type I, Type II, and gestational diabetes, other types of diabetes as recognized by the American Diabetes Association (See ADA Committee Report, Diabetes Care, 2003), hyperglycemia, impaired fasting glucose, impaired glucose tolerance, and pre-diabetes. "Tissue reflectance characteristic" includes any reflectance property of tissue that is useful in correction of detected light, including as examples the tissue reflectance at the Raman excitation wavelength, the tissue reflectance at the Raman scattering wavelength, and the tissue reflectance at other wavelengths found useful for estimating the tissue's intrinsic Raman scattering spectrum. A "measure of chemical change due to glycemic control" means any change in the chemical characteristics of tissue that is due to glycemic control, examples including concentration, measurements of the presence, concentration, or change in concentration of glycation end-products in tissue; measurements of the rate or change in the rate of the accumulation of such end-products; measurements of tissue membrane thickness or the change, rate of change, or direction of change of such thickness; tissue properties such as tensile strength, strain, or compressibility, or the change, rate of change, or direction of change of such property. A "measure of glycation end-product" means any measure of the presence, time, extent, or state of tissue associated with hyperglycemia, including, as examples, measurements of the presence, concentration, or change in concentration of glycation end-products in tissue; measurements of the rate or change in the rate of the accumulation of such end-products; measurements of the presence, intensity, or change in intensity of Raman scattering signal at Stokes shifts known to be associated with tissue glycation end-products; and measurements of the rate or change in the rate of the accumulation of such Raman signal. When light is described as having a "single wavelength," it is understood that the light can actually comprise light at a plurality of wavelengths, but that a significant portion of the energy in the light is transmitted at a single wavelength or at a range of wavelengths near a single wavelength.

BRIEF DESCRIPTION OF THE DRAWINGS

The drawings, which are not necessarily to scale, depict illustrative embodiments and are not intended to limit the scope of the invention.

DETAILED DESCRIPTION OF THE INVENTION

Figure 1:
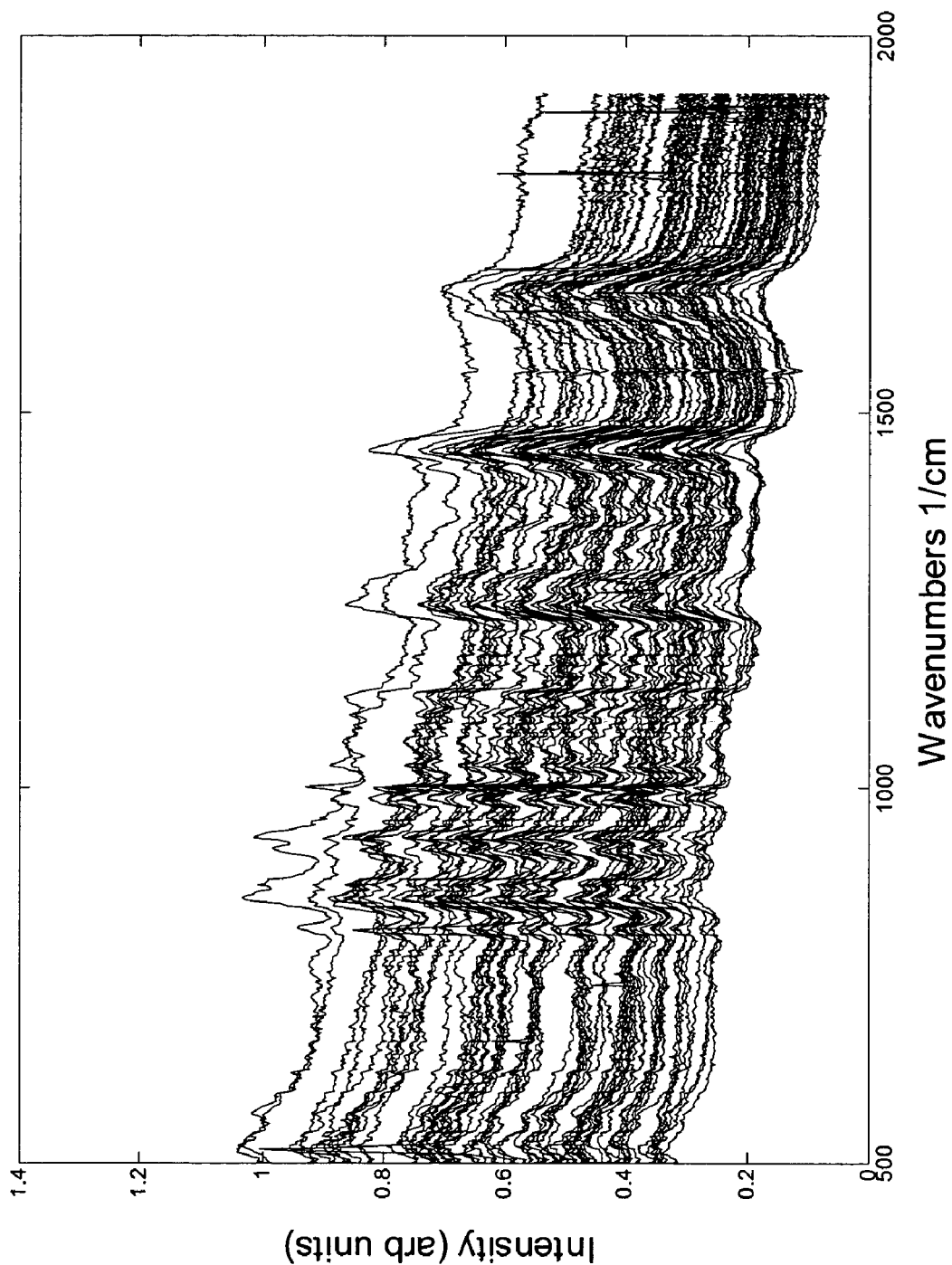
FIG. 1 is a graph of Raman spectra from 500-1900 wavenumbers, with an excitation wavelength of 785 nm.

Exposure of proteins to glucose generally leads to nonenzymatic glycation and glycoxidation, a process known as the Maillard reaction. The stable endproducts of the Maillard reaction are collectively denoted Advanced Glycation Endproducts (AGEs). In the absence of significant clearance, these AGEs accumulate at rates proportional to the average level of glycemia. The Maillard reaction can be viewed as an aging process that occurs routinely in health and at an accelerated rate in diabetics due to the presence of chronic hyperglycemia. In skin, collagen is the most abundant protein and readily undergoes glycation. Skin collagen AGEs commonly take the form of crosslinks and adducts; pentosidine (a crosslink) and carboxymethyl-lysine (CML, an adduct) are two well-studied examples of skin-collagen AGEs. Other examples of AGEs include fluorolink, pyrraline, crosslines, $N^\epsilon$ . . . -(2-carboxyethyl) lysine (CEL) glyoxal-lysine dimer (GOLD), methylglyoxal-lysine dimer (MOLD), 3DG-ARG imidazolone, vesperlysines A, B, C, and threosidine. Instruments and methods useful in Raman spectroscopy like that in the present invention have been described for other applications. See, e.g., Toshima et al., Jpn J Ophthalmol, 1990; Nie et al., Exp Eye Res, 1990 (evaluation of lens water content, and cataract progression); Sebag et al., Invest Ophthalmol Visual Sci, 1994 (evaluation of the progression of retinopathy); Shim and Wilson, J Raman Spectroscopy, 1996 (characterization of fundamental Raman-active bonds in skin); Caspers et al., Biospectoscopy, 1998 and Caspers et al., J Invest Derm, 2001, (study of natural moisturizing factor in stratum corneum); Caspers et al., Biophysical J, 2002 (Raman confocal microscopy of skin).

The relatively long half-life ($t_{1/2} \cong 15$ yr) of skin collagen and its associated AGEs make these species potential indicators of cumulative tissue glycemia. Levels of specific skin AGEs are correlated with the presence and severity of end-organ diabetes complications such as joint stiffness, retinopathy, nephropathy, and arterial stiffness. See Buckingham, *Diabetes Care,* 1984; Buckingham *J Clin Invest,* 1990; Monnier, *NEJM* 1986; Monnier, *J Clin Invest* 1986; Sell, *Diabetes,* 1992. In the largest such study to date, the DCCT Skin Collagen Ancillary Study Group evaluated a number of skin collagen variables from punch biopsies that were donated by a large fraction of the study's participants. These researchers found that skin AGEs were significantly correlated with the presence and clinical grade of diabetic neuropathy, nephropathy, and retinopathy. See Monnier et al., *Diabetes,* 1999.

The present invention can determine the diabetic state of a subject using one or more noninvasive Raman measurements. The invention can illuminate a portion of the tissue of the individual (e.g., a portion of the skin) with excitation light and detect Raman emission from the tissue. The characteristics of the Raman emission convey information about the disease state of the tissue under interrogation. The invention can apply additional processing algorithms to the measured Raman spectra before imposing a simple numerical threshold or a more detailed mathematical model to relate the optical information to disease state. In other embodiments, the output of the thresholding process or mathematical model can be a quantitative measure of diabetes-induced chemical change in the tissue of the individual being measured, rendered without regard to the individual's diabetic status. In additional embodiments, the invention can utilize a quantitative measure of diabetes-induced chemical changes in order to further infer or classify the diabetic status of the individual undergoing measurement.

Determining a Raman Emission of Tissue

Raman emission occurs when tissue inelastically scatters incident light. The wavelength difference between the incident and scattered light corresponds to the energy contributed to the vibrational energy of molecular constituents of the tissue. A Raman spectrum is the aggregate of wavelength-shifted, inelastically scattered radiation owing the specific structure and peaks to the chemical makeup of the tissue. Raman spectra convey specific information about the vibrational, stretching, and breathing bond energies of the illuminated sample. This molecular specificity provides insight into tissue composition and health. Detection of spectra features relating to advanced glycation endproducts is fundamental to screening and/or monitoring glucose-induced damage in the skin. While Raman spectroscopy is rich in information about the molecular composition of the tissue, it is minute in comparison to other optical phenomena such as fluorescence and Rayleigh (elastic) scattering. Line rejection filters (or similar) can be used to reduce interference from scattered incident light. Longer wavelength excitation sources can aid in reducing tissue fluorescence. Near infrared (NIR) excitation sources have the additional benefit of deeper penetration in tissue. Nevertheless, even using NIR excitation, tissue autofluorescence can be orders of magnitude more intense than the Raman scattering signal. Wavelength shift techniques or polynomial subtraction can be used to extract the comparatively weak Raman signal from the large, broad fluorescence spectra. See Shim and Wilson, J Raman Spectroscopy, 1997 and references cited therein.

When excitation light is launched into the tissue, it is subject to scattering and absorption processes that vary with the optical properties of the site under interrogation, the excitation wavelength, and the optical probe geometry. Emitted Raman light is also subject to wavelength- and location-dependent absorption and scattering as it propagates through the tissue prior to emergence and collection. Often, the tissue property of interest is its 'intrinsic' Raman emission, defined as the Raman emission that is scattered by a specimen that is homogeneous, nonscattering, and optically dilute. In order to accurately characterize the intrinsic Raman spectrum of the tissue of interest, the spectra-altering effects of scattering and absorption that are impressed upon the excitation and emitted light can be removed. Variations due to subject-to-subject and site-to-site differences can overwhelm the subtle spectral variations indicative of tissue status. Spectral correction based upon the tissue optics of each subject (at the same site as the Raman measurement, or at a different site having a predictable relationship to the site) can reveal the intrinsic Raman spectra of the molecules of interest. This intrinsic correction mitigates the variations across and within subjects, unmasking the spectral features relating to presence and state of disease.

The data described in this example were collected with a research Raman instrument based upon a 785 nm diode laser, a holographic transmission spectrometer and a CCD array detector. Residual fluorescence was removed by fitting a fifth-order polynomial to each Raman spectra. The polynomial acts as a wavelength-dependent baseline that is then subtracted to remove the predominant fluorescence.

Typical measured Raman spectra of skin are shown in FIG. 1. All spectra were obtained from in vitro porcine skin specimens. Individual specimens were excised from larger skin samples involved in an incubation experiment to assess accumulation of advanced glycation endproducts. The spectra represent Raman emission on both experimental and control samples over the course of a two-week study. Thus, spectra were acquired from skin residing in normoglycemic media as well as those immersed in hyperglycemic media and subject to AGE accumulation over the course of the study. The spectra demonstrate typical variations resulting from imperfect probe repositioning, environmental changes and subject-to-subject physiological differences. These variations can exceed the spectral variations due to disease state and hamper the diagnostic utility of the measured spectra. In order to accurately discriminate or quantify disease state, additional tissue-specific spectral corrections can be applied to obtain the intrinsic tissue Raman emission. One approximation for estimating the intrinsic spectrum, $E_{corr}$, involves dividing the measured Raman spectrum by the product of the roots of the measured reflectance at the excitation and/or emission wavelengths. See, e.g., Finlay et al., *Photochem Photobiol*, 2001, and Wu et al., *Appl Opt*, 1993:

$$E_{corr}(\lambda_x, \lambda_m) = \frac{E_{meas}(\lambda_x, \lambda_m)}{R_{meas}(\lambda_x)^k R_{meas}(\lambda_x)^n}; n, k < 1 \qquad \text{Eq 1}$$

The optimum values for n and k are dependent on the arrangement of source and detector fibers, and can be determined empirically.

If multiple spectra are collected from each sample at an acquisition session, then the spectroscopic insertion variation, $S_{insert}$, of the ith spectrum for specimen j can be expressed as the absolute deviation of that spectrum from the specimen's median:

$$S_{insert\,i,j}(\lambda,n,k) = abs[E_{corr_{i,j}}(\lambda,n,k) - \text{median}(E_{corr\cdot,j}(\lambda,n,k))]/\text{median}(E_{corr\cdot,j}(\lambda,n,k)). \qquad \text{Eq 4}$$

An aggregate measure of insertion variation is then the variance of $S_{insert}$:

$$v_{insert}(\lambda,n,k) = var(S_{insert}(\lambda,n,k)). \qquad \text{Eq 5}$$

Figure 2:
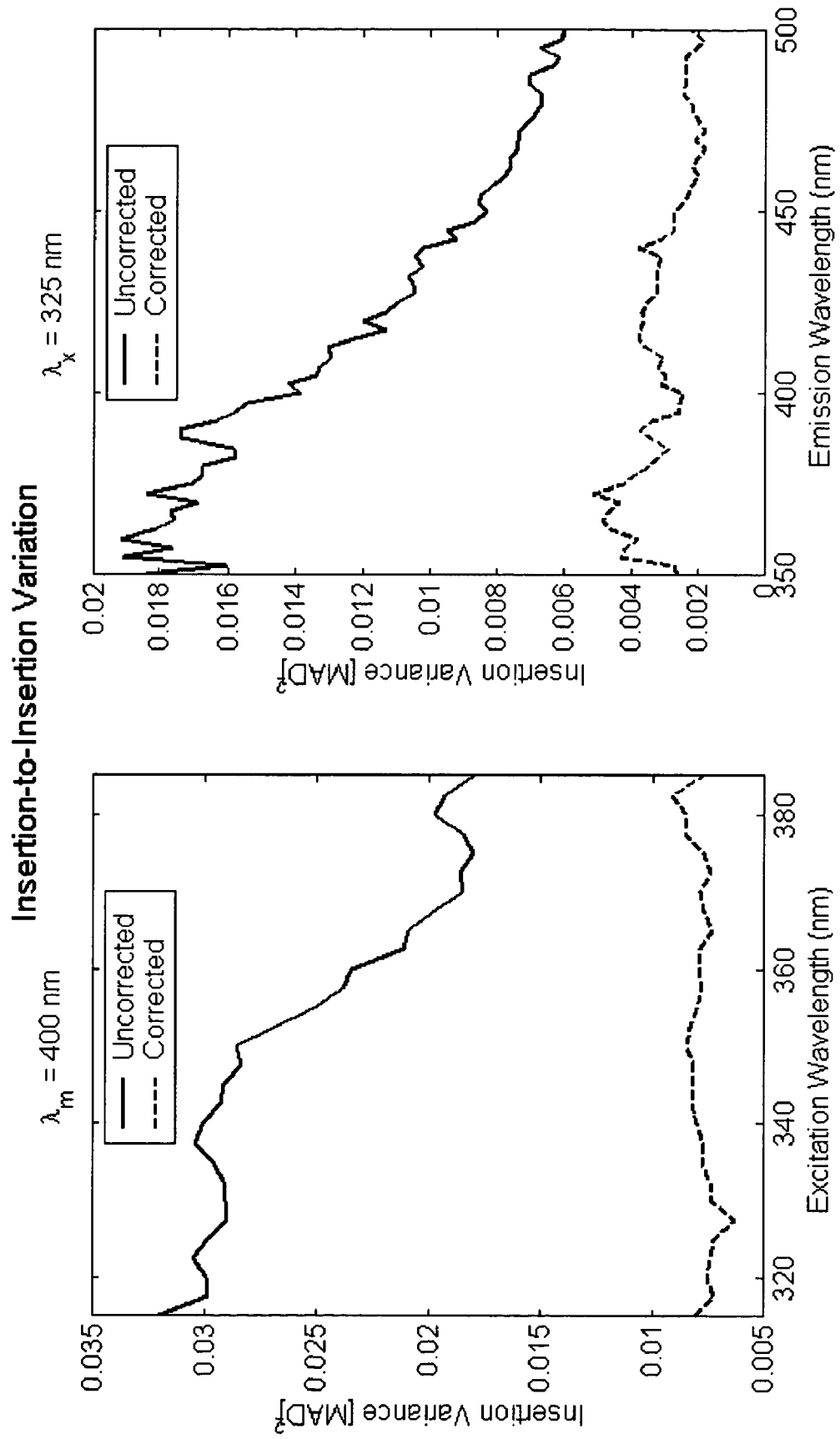
FIG. 2 is an example, performed with fluorescence spectra, of the insertion variance of the measured (solid lines, 'uncorrected') and intrinsic-corrected spectra (dashed lines, k=0.5, n=0.7).

FIG. 2 depicts the insertion variance of the measured (solid lines, 'uncorrected') and intrinsic-corrected spectra (dashed lines, k=0.5, n=0.7) for a set of fluorescence spectra obtained from 17 diabetic and 17 non-diabetic subjects between the ages of 40 and 60 years. It can be seen that the intrinsic correction process reduces the insertion variance by approximately a factor of four over the full wavelength range. Under the presumption that the intrinsic spectrum of the tissue does not change from insertion to insertion, this procedure mitigates a portion of the corrupting effects of variation in tissue optical properties.

A variety of other procedures can accomplish intrinsic spectral correction. For example, a number of methods by which the measured spectra can be corrected using knowledge of the measured reflectance, tissue optical properties, and probe-dependent parameters can be used with the present invention. See, e.g., Gardner et al., *Appl Opt*, 1996, Zhang et al., *Opt Lett*, 2000; Muller et al., *Appl Opt*, 2001. In addition, intrinsic corrections can be made using a procedure in which the correction parameters for a given probe are created by measuring one or more tissue phantoms for which the emission, absorption, and scattering properties have been well characterized. This procedure can also be accomplished via Monte-Carlo or other computer simulation of the optical probe's response to media with known optical properties.

Any of these processes can be used to correct for the effects of tissue optical properties in noninvasive skin Raman emission measurements.

While the examples described here generally concern steady-state Raman measurements without regard to polarization, it is possible to apply these methods to other Raman spectroscopy measurement modalities. For example, Fourier-transform Raman spectroscopy (FT Raman) in which the Raman emission is detected interferometrically can be suitable. Another suitable approach involves time-resolved techniques, in which a short burst of excitation light is applied to the tissue, and the Raman emission is time-gated as means to reject the 'slower' fluorescence. In addition, any of these techniques can be used in conjunction with an imaging methodology such as microscopy or macroscopic scanning of the excitation beam in order to acquire information about the spatial information. Any of the above-mentioned methods can be used in conjunction with a measurement technique that allows depth discrimination, such as a confocal detection system or optical coherence tomography, to add information concerning the distribution of Raman-active constituents with respect to depth beneath the tissue surface. The preceding discussion primarily describes detection of spontaneous Raman scattering as the means for gathering noninvasive, spectroscopic information relating to the disease state of the tissue. Other Raman techniques can also be incorporated in the invention. Examples of these alternative techniques are resonance Raman spectroscopy, surface-enhanced Raman scattering (SERS), anti-Stokes Raman scattering and coherent anti-Stokes Raman spectroscopy (CARS).

Determining a Model Relating Raman Properties to Disease State or Chemical Changes The relationship between tissue Raman spectral properties at one or more wavelengths and diabetes disease state is typically not apparent upon visual inspection of the spectral data. Because this is the case, it is usually necessary that a multivariate mathematical relationship, or 'model', be constructed to classify tissue disease states or to quantify chemical changes using intrinsic Raman spectra. The construction of such a model generally occurs in two phases: (i) collection of 'calibration' or 'training' data, and (ii) establishing a mathematical relationship between the training data and the disease states or reference concentrations represented in the training data.

During the collection of training data, it can be desirable to collect Raman data from many individuals, representing disease states or reference values one wishes to characterize with the model to be constructed. For example, if one wishes to construct a model that separates diabetics from nondiabetics, it can be desirable to collect representative spectra from a wide variety of both types of individuals. It can be important to collect these data in a manner that minimizes the correlation between disease state and other parameters that can result in spectral variation. For example, the natural formation of collagen AGEs in health results in a correlation between skin AGE content and chronological age. It can be important, therefore, to obtain spectra from diabetics and nondiabetics spanning the ages for which the classification model is desired to be applicable. Alternatively, if one wished to construct a model that quantified the level of a specific skin collagen AGE, it can be advisable to collect spectroscopic data spanning a wide range of AGE reference values each day rather than to measure all individuals having the smallest AGE concentrations early in the study and all individuals with larger AGE concentrations later in the study. In the latter case, a spurious correlation arises between AGE concentration and time, and if there are instrumental trends over the course of the study, the resulting model might be calibrated to instrument state rather than analyte concentration.

As the training data are collected, additional reference information can be collected in order to later construct an appropriate classification model. For example, if the classification model is to predict diabetic state, the diabetes status of some or all of the individuals represented in the training set can be collected and associated with the corresponding spectroscopic training data. Alternatively, the classification model can predict the level of a certain chemical species in the skin, such as glycated collagen, glycated elastin, a specific AGE such as pentosidine or CML, or other proteins modified by the hyperglycemic conditions associated with diabetes mellitus. In these cases, skin biopsy specimens can be collected from individuals during the collection of training data. In addition, if other ancillary information, such as age, body mass index, blood pressure, HbA1c, etc. is to be used in generating later disease state assessments, this information can be collected for some or all spectra in the training set.

After the training data are collected, a multivariate model can be constructed to relate the disease states associated with the training data to the corresponding spectroscopic information. The exact model can be chosen based upon the ultimate goal of the training phase. There are at least two types of multivariate models that one might construct. In the first, the goal of the training process is to create a model that correctly classifies the disease state of the measured tissue. In this case, the output of the model is an assignment to one or more discrete classes or groups. These classes or groups might represent different grades or manifestations of a particular disease. They might also represent various degrees of risk for contracting a particular disease or other subgroups of the population that are pertinent to the disease state in question. For the second model type, the goal is to provide a quantitative estimate of some diabetes-induced chemical change in the system. The output of this model can be continuously variable across the relevant range of variation and is not necessarily indicative of disease status.

Classification of Tissue Disease Status

Figure 3:
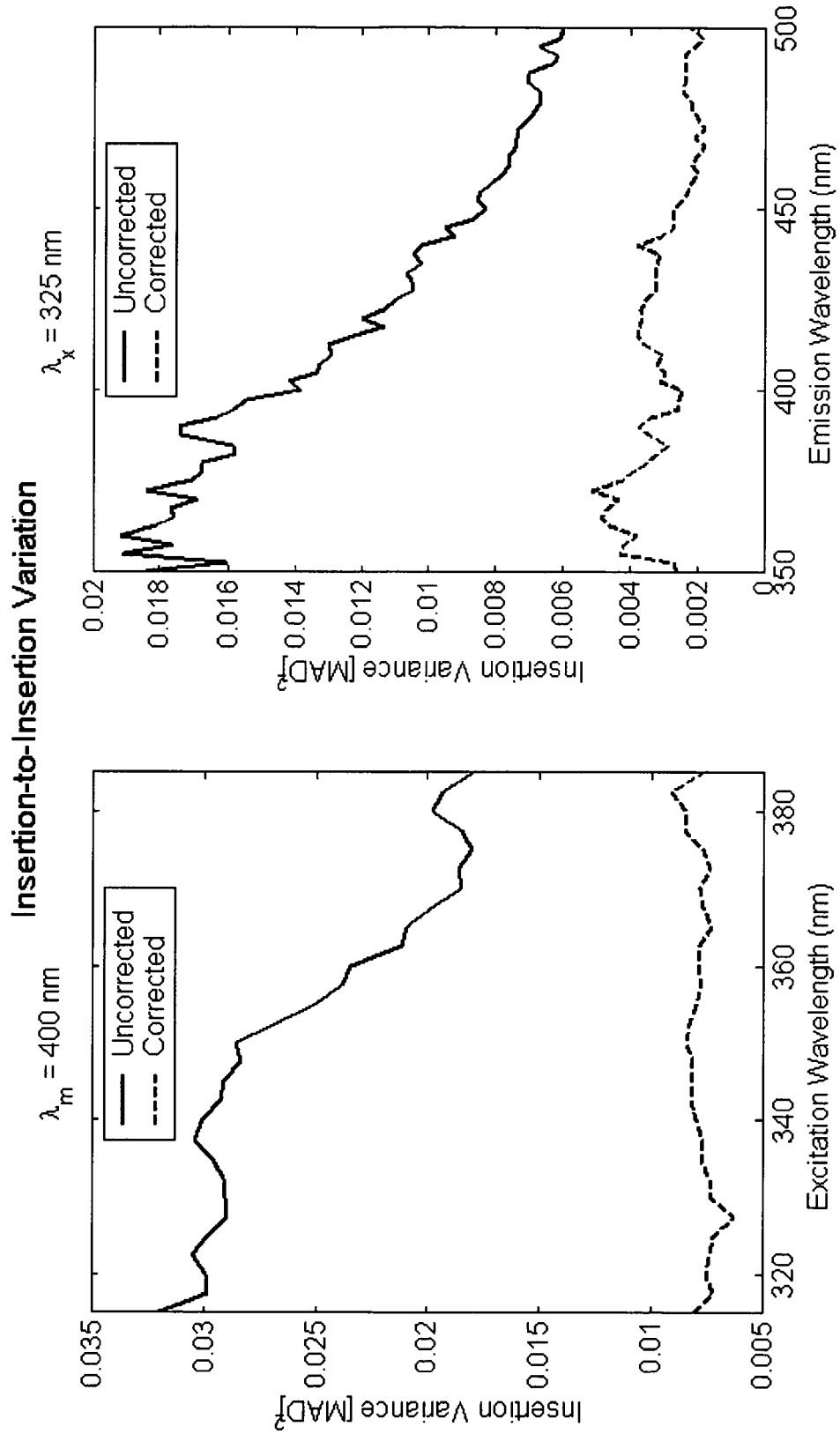
FIG. 3 is a diagrammatic representation of model-building steps.

Model-building steps that can be followed when the end goal is to use the model to assess tissue disease state are depicted diagrammatically in FIG. 3. The first step, spectral preprocessing, involves pre-treatment, if any, of the spectral data including, for example, background-correction and intrinsic-Raman correction steps as described above. In the second step, the dimensionality of the data set can be reduced by employing a factor analysis method. Factor analysis methods allow an individual spectrum to be described by its scores on a set of factors rather than the spectral intensities at each collected wavelength. A variety of techniques can be utilized in this step; Principal Components Analysis (PCA) is one suitable method. The factors generated, for example, by Partial Least-Squares (PLS) regression onto a reference variable associated with disease status can also be used. After the factors have been generated, those factors that are most useful for classification can be selected. Valuable factors typically exhibit a large separation between the classes while having low within-class variance. Factors can be chosen according to a separability index; one suitable method for calculating the separability index for factor f is:

$$Separability_f = \frac{|\bar{x}_{1,f} - \bar{x}_{2,f}|}{s_{1,f}^2 + s_{2,f}^2},\qquad\text{Eq 6}$$

where $\bar{x}_{1,f}$ is the mean score for class 1, $\bar{x}_{2,f}$ is the mean score for class 2, and $S^2$ represents variance of the scores within a class.

Figure 4:
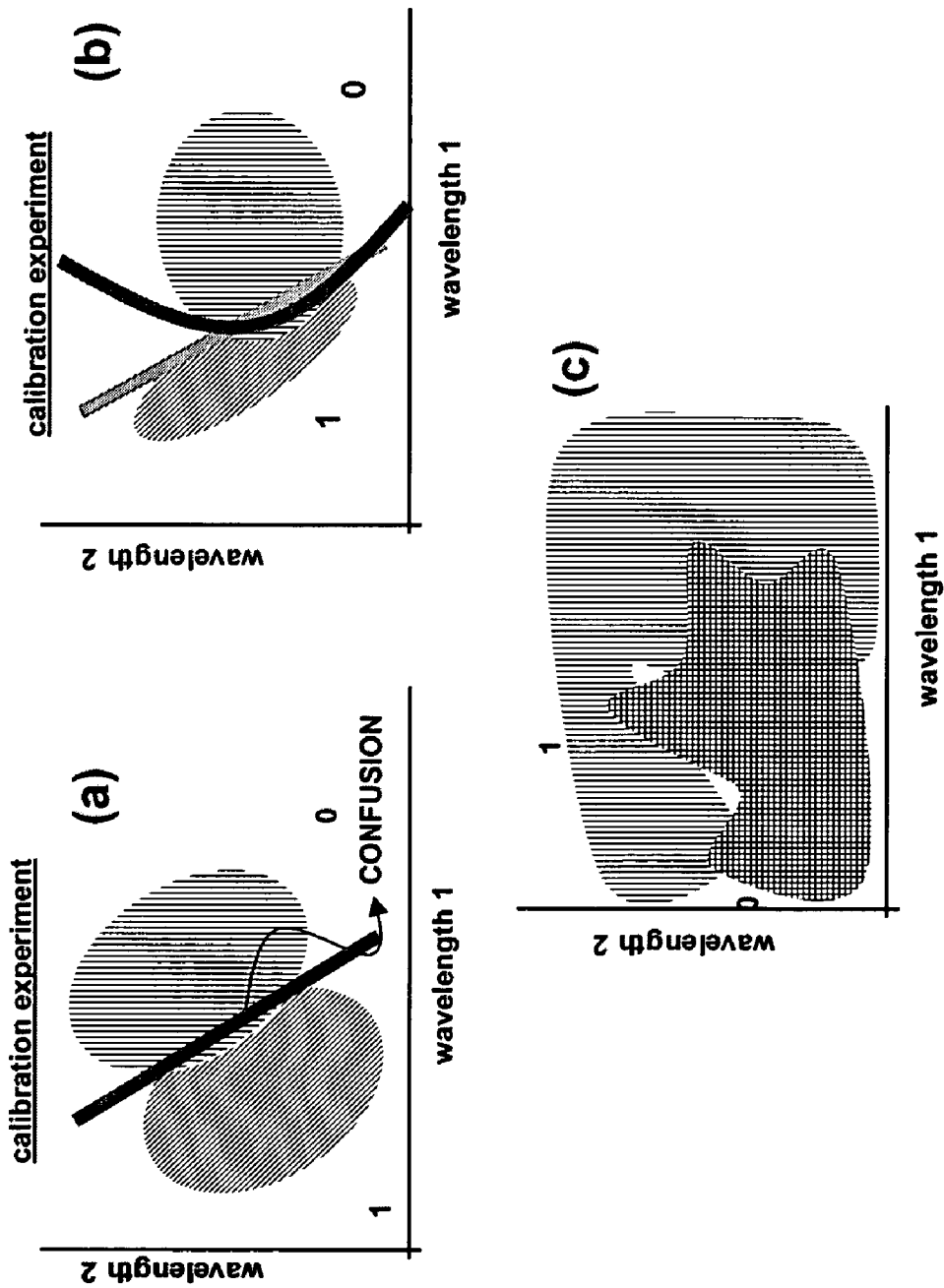
FIG. 4 is an illustration of the manner in which a discriminant function might find the best separation between two groups.

Finally, a technique for separating the data into the various classes can be selected. A variety of algorithms can be suitable, and the optimum algorithm can be selected according to the structure of the training data. In Linear Discriminant Analysis (LDA), a single linear function that best separates the multidimensional spectroscopic data into the reference classes observed in the training period is constructed. In Quadratic Discriminants Analysis, a quadratic discriminant function is constructed. FIG. 4 illustrates the manner in which the discriminant function might find the best separation between two groups—it depends on the structure of the data. In some cases (FIG. 4(a)), a linear discriminant function is sufficient to separate the classes. As the multi-dimensional structure of the classes becomes more complex, however, more sophisticated classifiers, such as quadratic functions, are required (FIG. 4(b)). In some situations (FIG. 4(c)), the structure of the data makes even quadratic discriminant analysis difficult and other classification methods can be more appropriate.

A number of suitable classification algorithms exist. For example, k-nearest neighbors, logistic regression, hierarchical clustering algorithms such as Classification and Regression Trees (CART), and machine learning techniques such as neural networks, can all be useful and appropriate techniques. See, e.g., Huberty, *Applied Discriminant Anaylsis*, Wiley & Sons, 1994 and Duda, Hart, and Stork, *Pattern Classification*, Wiley & Sons, 2001.

Quantitation of Diabetes-induced Chemical Modifications

If the end goal is to quantify the concentration of an analyte or a class of analytes embedded in the tissue, a different approach can be taken in the model-building process. In this case, a set of (typically continuous) reference values for the analyte(s) in question can be obtained for some or all spectra in the training set. For example, in the event that the model is to quantify the level of CML in skin collagen, the reference concentrations associated with each spectrum in the training set can come from CML assays conducted on skin punch biopsy specimens obtained during calibration. In the event that the biopsy process is too invasive for the study participants, some surrogate for AGE-related chemical changes can also be used. For example, under the assumption that FPG values increase as the degree of diabetes progression increases, a reasonable compromise can collect FPG data as a surrogate for skin AGE concentration. HbA1c and OGTT information can be used similarly.

Calibration models used to predict quantitative values associated with a test set can be constructed by forming a mathematical relation between reference values and associated spectral data. A variety of algorithms are suitable. For example, in Principal Components Regression (PCR) the calibration data are first decomposed into a set of orthogonal scores and loadings, and then the reference values are regressed onto the scores of the first N PCA factors. Another suitable method is Partial Least-Squares (PLS) regression, in which a set of factors is constructed so that the squared covariance between the reference values and the scores on each successive PLS loading vector is maximized. These procedures and others have been summarized by Martens and Naes in Multivariate Calibration, Wiley & Sons (1989).

Quantitative calibration models other than the regression techniques described here can also be suitable for use with the present invention. Those skilled in the art will recognize that a variety of other approaches are available, including neural networks and other nonlinear techniques.

Determining Disease State or Chemical Changes from Raman Spectroscopy

After model construction, Raman spectral measurements can be made on new specimens having an unknown disease state or diabetes-related chemical change. The method by which the disease state or chemical properties of the new specimen are determined can depend on the type of model constructed in the training phase.

Classification of Tissue Disease Status

As mentioned above, a variety of models are available for discrimination of various diabetic states from measured Raman spectra. For example, when the method of Quadratic Discriminants Analysis is used, the new Raman spectrum is projected onto the factors created with the training data during construction of the classification model, creating a new vector of scores, $x_i$, for the test spectrum. The means $\bar{x}_j$ and covariance matrices $S_j$ of the scores of the training set over the previously selected factors are computed for each class j. For example, j=1,2 for a two-class (i.e., diabetic vs. non-diabetic) problem. The Mahalanobis distance, $D_{i,j}$ from sample i to class j, then is computed for each vector of scores ($x_i$) by $$D_{i,j}=(x_i-\bar{x}_j)^T S_j^{-1}(x_i-\bar{x}_j).\qquad\text{Eq 7}$$

The posterior probability that test sample i is a member of class j, p(i∈j), can be calculated using Equation 8. As with all probabilities, this number ranges between 0 and 1; probabilities close to 1 indicate that an observation lies close to the diabetic class, and probabilities close to 0 indicate that an observation lies close to the non-diabetic class. The probability that sample i is a member of class j is given by $$p(i \in j) = \frac{\pi_{ij} e^{-D_{ij}/2}}{\sum_j \pi_{ij} e^{-D_{ij}/2}},\qquad\text{Eq 8}$$

where $\pi_{ij}$ are the prior probabilities that test sample i is a member of class j based on other knowledge (risk factors, etc.). The prior probabilities are parameters that can be tuned in the prediction phase depending, in part, on the diagnostic application of the classification algorithm.

Finally, a threshold can be applied that assigns the new Raman spectral measurement to a particular tissue disease state. For example, it might be determined that all Raman measurements yielding a posterior probability of diabetes greater than 0.75 will be assigned to the diabetic class. Like the prior probabilities, the exact threshold applied in validation can depend on a variety of factors, including the application, disease prevalence, and socioeconomic ramifications of positive and negative test results.

Quantitation of Diabetes-Induced Chemical Modifications

The output of a quantitative calibration model can be a regression vector that converts the corrected Raman spectrum into a quantitative analyte prediction via an inner product:

$$\hat{a}=F_{corr} \circ b,\qquad\text{Eq 9}$$

where â is the analyte prediction and b is the regression vector.

The method for generating a quantitative output can vary with the model constructed in the training phase. Final analyte quantitation with, for example, a neural network proceeds by a different process but yields a similar output.

After the construction of either type of multivariate model (i.e., a quantitative model for chemical change or a classification model for tissue disease state), the accuracy of the model can be tested by predicting the disease status associated with well-characterized 'validation' spectra. A variety of techniques also exists for accomplishing this task. In leave-one-out cross-validation, a single spectrum or set of spectra from the training set are omitted from the model-building process, and then the resulting model is used to predict the disease status associated with the spectra left out of the model. By repeating this process a sufficient number of times, it is possible to develop a mathematical estimate of the performance of the model under new conditions. A more rigorous test of the newly constructed model is to apply the model to an entirely new data set, or a 'test' set. In this case, the disease status associated with each spectrum is known, but the 'test' spectra are collected at a different time (e.g., subsequent to model-building) than the training data. By comparing the predictions on the 'test' data to the reference values associated with these data, the diagnostic accuracy of the model in question can be assessed independent of the training data.

EXAMPLE APPARATUS

Figure 5:
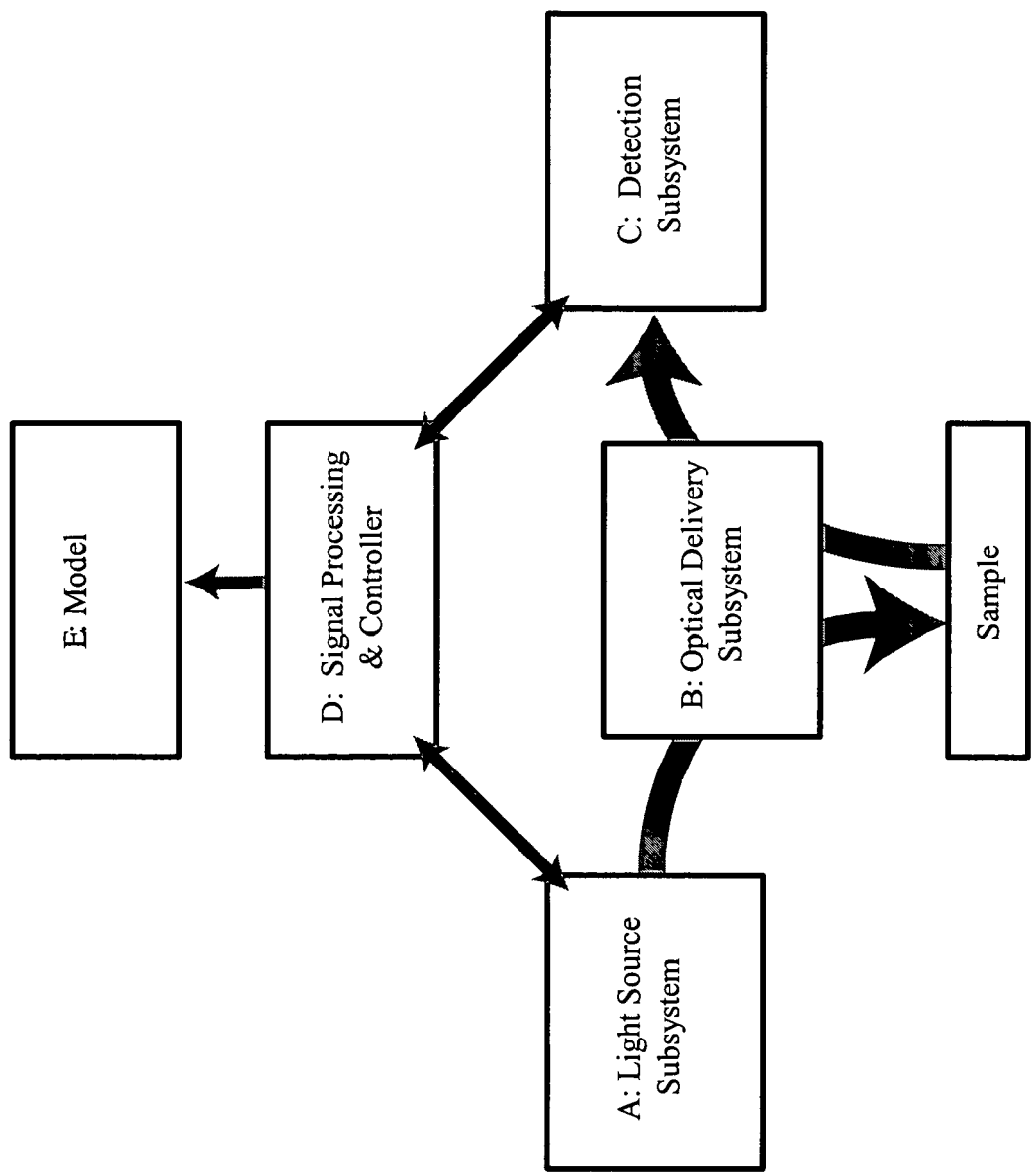
FIG. 5 is a schematic representation of components or sub-systems of an apparatus according to the present invention.

Components or sub-systems of an apparatus to characterize and/or quantify disease state by tissue Raman emission are illustrated in FIG. 5. An illumination subsystem comprises a light source A suitable to illuminate the tissue and thereby induce Raman scattering within the tissue. Illumination subsystem includes an optical system B that couples the light produced by the light source A to the tissue and collects the resulting Raman emission light from the tissue sample and couples the collected Raman emission to a detection sub-system C. In the detection subsystem, the Raman emission is typically converted into an electrical signal. The signal corresponding to the tissue Raman emission is measured and characterized by an analysis or data processing and control system D. The processing/control system can also control or modify the actions of the other sub-systems.

Figure 6:
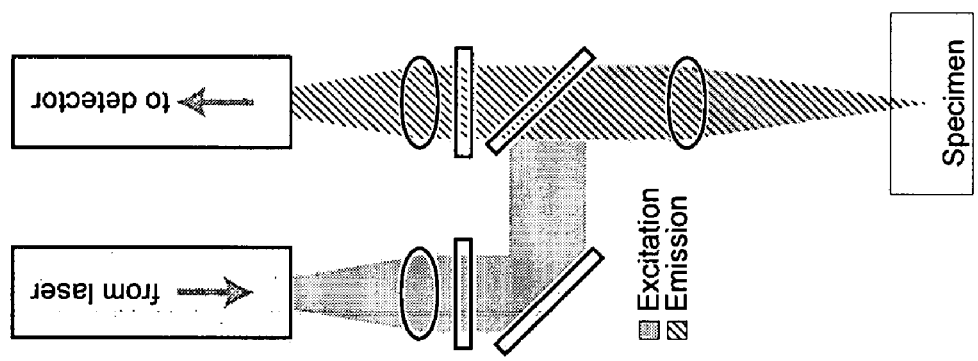
FIG. 6 is a schematic depiction of a Raman fiber probe suitable for use in the present invention.

Example I of such a system embodies a continuous-wave diode laser as the light source. The optical-coupling sub-system is comprised of a fiber probe that couples the excitation light to the tissue and collects Raman scattering emanating from the tissue, as illustrated in FIG. 6. The probe incorporates a line-pass filter to reject Raman emission of the fiber itself, as well as rejecting any broad spontaneous emission from the diode laser (i.e., the filter only passes the narrow bandwidth of the laser). A pair of dichroic mirrors creates a coaxial path for excitation and emission. A final lens focuses the excitation radiation and then collects and collimates Raman emission. The Raman emission passes through the second of the dichroic pair and a line blocking filter rejects Rayleigh scattered excitation final. A lens couples the Raman emission into a fiber or fiber bundle for relay to the detection system. The detection system contains a spectrograph and a detector such as a CCD array. The electrical signal corresponding to the tissue Raman emission is digitized, processed and stored by a computer (Component D). The computer also controls functions of other sub-systems such as the spectrograph and shutters.

In Example II, the fiber-optic probe of Example I is replaced by a system of lenses and mirrors to convey excitation light from the light source to the tissue and then collect Raman emission from the tissue and relay it to the detection sub-system.

In Example II, the continuous-wave laser is replaced by a pulsed, modulated or mode-locked laser.

In Example III, the diode laser is replaced by a solid-state or gas laser.

In Example V, the detection system of Example I comprised of a spectrograph and an array detector is replaced by a monochromator and a photomultiplier.

Figure 7:
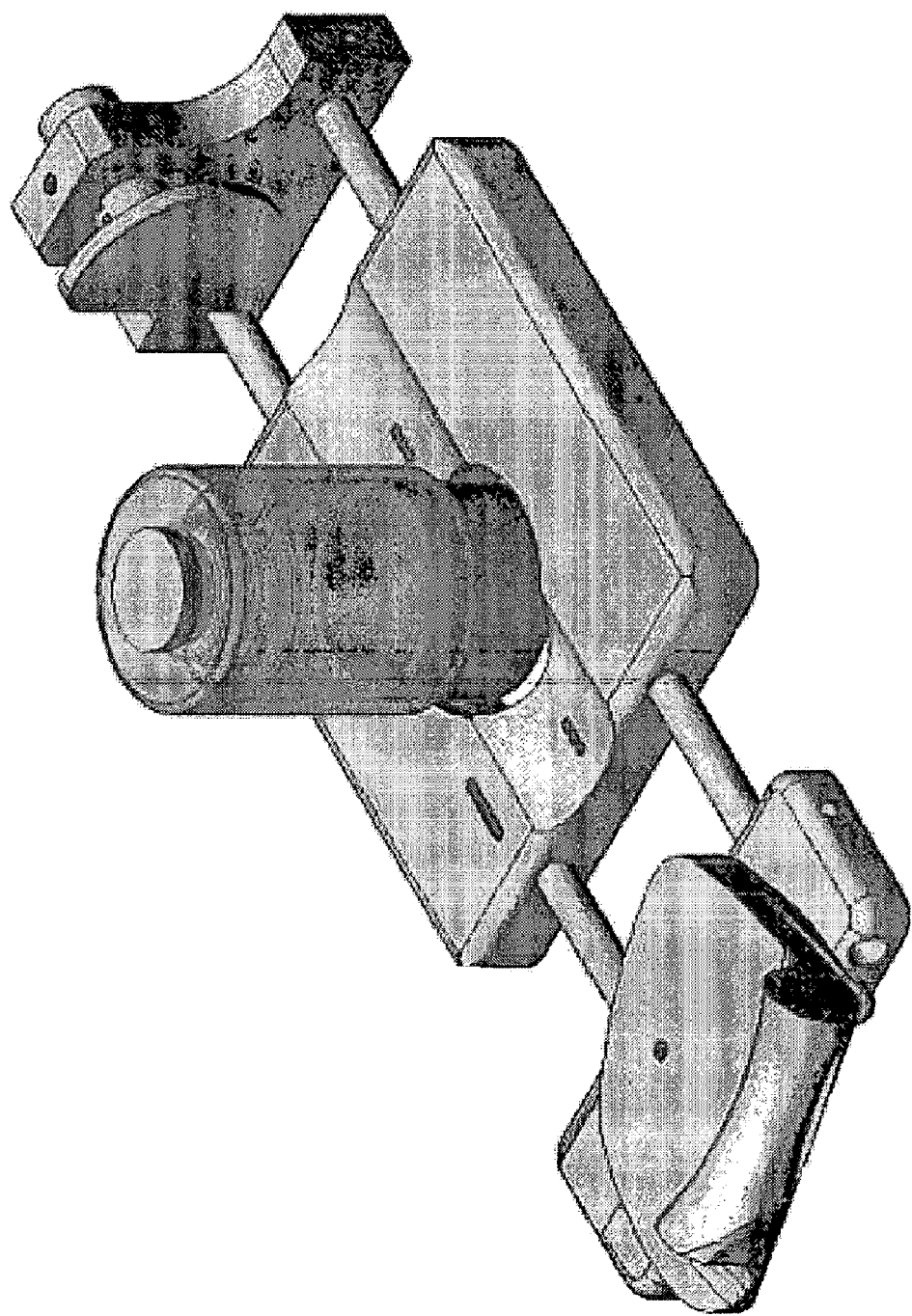
FIG. 7 is an illustration of a tissue interface suitable for use in the present invention.

An example of a fixture—in this instance, a forearm cradle—to hold the fiber bundle in contact with the skin of the subject is shown in FIG. 7. The cradle provides a means for the subject to comfortably rest their arm while the underside forearm skin is in contact with the delivery/collection end of the fiber bundle. The cradle also facilitates reproducible positioning of the volar forearm site with respect fiber optic bundle. The Raman emission collected by the detector fiber (s) are coupled to the detection system as depicted in FIG. 5, item C. The spectrograph disperse filters the incoming Raman emission upon the detector array. The signal from the CCD array is digitized and recorded by a computer that also tunes the gratings, adjusts detector and controls the optical shutters.

Those skilled in the art will recognize that the present invention can be manifested in a variety of forms other than the specific embodiments described and contemplated herein. Accordingly, departures in form and detail can be made without departing from the scope and spirit of the present invention as described in the appended claims.

What we claim is:

1. A method of determining a disease state in an individual, where "determining a disease state" comprises determining the presence or likelihood of diabetes; the degree of progression of diabetes; a change in the presence, likelihood, or progression of diabetes; a probability of having, not having, developing, or not developing diabetes; the presence, absence, progression, or likelihood of complications from diabetes, and where "determining a disease state" does not comprise measurement of glucose concentration, the method comprising:
   a. illuminating a portion of the tissue of the individual with excitation light;
   b. detecting light emitted from the tissue by Raman scattering of a chemical within the tissue;
   c. acquiring biologic information relating to the individual; and
   d. determining the disease state from the information, the detected light, and a model relating biologic information, Raman scattering and disease state.

2. A method as in claim 1, wherein the excitation light has a first wavelength at a first time, and a second wavelength, different from the first wavelength, at a second time.

3. A method as in claim 1, wherein detecting light emitted from the tissue comprises detecting light at each of a plurality of wavelengths.

4. A method as in claim 3, wherein the excitation light has a single wavelength, and wherein detecting light emitted from the tissue comprises detecting light at a plurality of wavelengths.

5. A method as in claim 1, wherein detecting light emitted from the tissue comprises:
   a. determining a tissue reflectance characteristic at an excitation light wavelength;
   b. detecting light returned from the tissue in response to illumination at the excitation wavelength;
   c. determining a corrected Raman measurement from the detected light and the tissue reflectance characteristic;

d. and wherein determining the disease state comprises determining the disease state from the corrected Raman measurement and a model relating Raman scattering and disease state.

6. A method as in claim 1, wherein detecting light emitted from the tissue comprises:
   a. determining a tissue reflectance characteristic at a detection wavelength;
   b. detecting light at the detection wavelength returned from the tissue in response to illumination;
   c. determining a corrected Raman measurement from the detected light and the tissue reflectance characteristic;
   d. and wherein determining the disease state comprises determining the disease state from the corrected Raman measurement and a model relating Raman scattering and disease state.

7. A method as in claim 1, wherein detecting light emitted from the tissue comprises:
   a. determining a first tissue reflectance characteristic at an excitation light wavelength;
   b. determining a second tissue reflectance characteristic at a detection wavelength;
   c. detecting light at the detection wavelength returned from the skin in response to illumination at the excitation wavelength;
   d. determining a corrected Raman measurement from the detected light and the first and second tissue reflectance characteristics;
   e. and wherein determining the disease state comprises determining the disease state from the corrected Raman measurement and a model relating Raman scattering and disease state.

8. A method as in claim 5, wherein determining a tissue reflectance characteristic comprises:
   a. illuminating the tissue with reflectance illumination light having an excitation wavelength;
   b. detecting reflectance light having the excitation wavelength reflected from the skin, using the same detector as used to detect light returned from the tissue; and
   c. establishing a tissue reflectance characteristic from a relationship between the reflectance illumination light and the reflectance light.

9. A method as in claim 5, wherein determining a tissue reflectance characteristic comprises:
   a. illuminating the portion of the tissue with reflectance illumination light having an excitation wavelength;
   b. detecting reflectance light having the excitation wavelength reflected from the portion of the skin; and
   c. establishing a tissue reflectance characteristic from a relationship between the reflectance illumination light and the reflectance light.

10. A method as in claim 6, wherein determining a tissue reflectance characteristic comprises:
    a. illuminating the tissue with reflectance illumination light having a wavelength the same as the detection wavelength;
    b. detecting reflectance light having the detection wavelength reflected from the skin, using the same detector as used to detect light returned from the tissue; and
    c. establishing a tissue reflectance characteristic from a relationship between the reflectance illumination light and the reflectance light.

11. A method as in claim 6, wherein determining a tissue reflectance characteristic comprises:
    a. illuminating the portion of the tissue with reflectance illumination light having a wavelength the same as the detection wavelength;
    b. detecting reflectance light having the detection wavelength reflected from the portion of the skin; and
    c. establishing a tissue reflectance characteristic from a relationship between the reflectance illumination light and the reflectance light.

12. A method as in claim 1, wherein detecting light comprises determining a relationship between an excitation wavelength and Raman emission at a detection wavelength, and wherein determining disease state comprises comparing the relationship with a model defining a relationship between disease state and relationships between the excitation wavelength and Raman emission at the detection wavelength.

13. A method as in claim 12, wherein detecting light comprises determining a relationship between illumination at an excitation wavelength and Raman emission at a plurality of detection wavelengths, and wherein determining disease state comprises comparing the relationship with a model defining a relationship between disease state and relationships between the excitation wavelength and Raman emission at the plurality of detection wavelengths.

14. A method as in claim 12, wherein detecting light comprises determining a relationship between illumination at a plurality of excitation wavelengths and Raman emission at a plurality of detection wavelengths, and wherein determining disease state comprises comparing the relationship with a model defining a relationship between disease state and relationships between the plurality of excitation wavelengths and Raman emission at the plurality of detection wavelength.

15. A method as in claim 1, wherein the biologic information comprises age of the individual, height of the individual, weight of the individual, history of disease in the individual's family, ethnicity, skin melanin content, laser-Doppler information from the subject's tissue, or a combination thereof.

16. A method as in claim 1, wherein the tissue comprises the skin of the individual.

17. A method as in claim 1, wherein the model is determined according to:
    a. for each of a plurality of subjects:
       i. determining a Raman emission property of a portion of the tissue of the subject;
       ii. determining a disease state of the subject;
    b. applying a multivariate method to the plurality of Raman emission property determinations and associated disease state determinations to generate a model relating Raman emission property to disease state.

18. A method of determining a disease state in an individual, where "determining a disease state" comprises determining the presence or likelihood of diabetes; the degree of progression of diabetes; a change in the presence, likelihood, or progression of diabetes; a probability of having, not having, developing, or not developing diabetes; the presence, absence, progression, or likelihood of complications from diabetes, and where "determining a disease state" does not comprise measurement of glucose concentration, the method comprising:
    a. establishing an interface between a optical system and a portion of the skin of the individual;
    b. determining a relationship of illumination light at an excitation wavelength and the response of the skin at a detection wavelength for each of a plurality of pairings of excitation wavelength and detection wavelength;
    c. determining a tissue reflectance property of the skin at each of the illumination wavelengths and at each of the detection wavelengths;
    d. determining a measure of the intrinsic Raman emission of the skin from the relationships of illumination light and detected light and the tissue reflectance properties;

e. acquiring biologic information relating to the subject; and f. determining the disease state of the individual from the information, the intrinsic Raman emission, and a model relating intrinsic biologic information, Raman emission and disease state.

19. A method as in claim 18, wherein the biologic information comprises information from fluorescence spectroscopic investigation of the subject.

20. A method as in claim 18, wherein the biologic information comprises age of the subject, height of the subject, weight of the subject, history of disease in the subject's family, ethnicity, skin melanin content, blood HDL cholesterol level of the subject, blood LDL cholesterol level of the subject, blood triglycerides level of the subject, or a combination thereof.

21. A method of determining a model relating biologic information, Raman emission and disease state, where "disease state" comprises the presence or likelihood of diabetes; the degree of progression of diabetes; a change in the presence, likelihood, or progression of diabetes; a probability of having, not having, developing, or not developing diabetes; the presence, absence, progression, or likelihood of complications from diabetes, and where "determining a disease state" does not comprise measurement of glucose concentration, the method comprising:

a. for each of a plurality of subjects:
      i. determining a Raman emission property of a portion of the tissue of the subject;
      ii. acquiring biologic information from the subject;
      iii. determining a disease state of the subject;
    b. applying a multivariate method to the plurality of Raman emission property determinations, biologic information acquisitions, and associated disease state determinations to generate a model relating biologic information and Raman emission property to disease state.

22. A method as in claim 21, wherein determining a Raman emission property comprises determining an intrinsic Raman emission of the portion of the tissue.

23. A method as in claim 21, wherein determining a Raman emission property comprises determining an intrinsic Raman emission of the portion of the tissue at each of a plurality of detection wavelengths responsive to excitation light having an excitation wavelength.

24. A method as in claim 21, wherein determining a Raman emission property comprises determining an intrinsic Raman emission of the portion of the tissue at pairings of a plurality of detection wavelengths and a plurality of excitation wavelengths.

25. A method as in claim 21, wherein determining a Raman emission property of a portion of the tissue of the subject comprises:

a. illuminating the portion of the tissue of the individual with excitation light;
    b. detecting light emitted from the tissue by Raman emission of a chemical within the tissue;

26. A method as in claim 25, wherein detecting light emitted from the tissue comprises:

a. determining a tissue reflectance characteristic at an excitation light wavelength;
    b. detecting light returned from the tissue in response to illumination at the excitation wavelength;
    c. determining a corrected Raman emission measurement from the detected light and the tissue reflectance characteristic.

27. A method as in claim 25, wherein detecting light emitted from the tissue comprises:

a. determining a tissue reflectance characteristic at a detection wavelength;
    b. detecting light at the detection wavelength returned from the tissue in response to illumination;
    c. determining a corrected Raman emission measurement from the detected light and the tissue reflectance characteristic.

28. A method as in claim 25, wherein detecting light emitted from the tissue comprises:

a. determining a first tissue reflectance characteristic at an excitation light wavelength;
    b. determining a second tissue reflectance characteristic at a detection wavelength;
    c. detecting light at the detection wavelength returned from the skin in response to illumination at the excitation wavelength;
    d. determining a corrected Raman emission measurement from the detected light and the first and second tissue reflectance characteristics.

29. A method as in claim 21, wherein determining the disease state comprises at least one of:

a. evaluating the subject according to an OGTT;
    b. evaluating the subject according to an FPG;
    c. evaluating the subject according to an HbA1c test;
    d. determining a level of glycation endproducts in the tissue of the subject.

30. A method as in claim 21, wherein the tissue is not the eye, and wherein applying a multivariate method comprises applying a multivariate model constructed using ordinary least-squares(OLS), Partial Least Squares (PLS), Principal Components Regression (PCR), a Tikhonov-regularized least-squares model, or a combination thereof.

31. A method as in claim 21, wherein the portion of the tissue comprises the skin of the subject.

32. An apparatus for the determination of disease state in an individual, where "disease state" comprises the presence or likelihood of diabetes; the degree of progression of diabetes; a change in the presence, likelihood, or progression of diabetes; a probability of having, not having, developing, or not developing diabetes;

the presence, absence, progression, or likelihood of complications from diabetes, and where "determining a disease state" does not comprise measurement of glucose concentration, the apparatus comprising:
    a. an illumination subsystem;
    b. a detection subsystem;
    c. an analysis subsystem, comprising a model relating biologic information and Raman emission property of the skin of an individual to disease state.

33. An apparatus as in claim 32, wherein the model is determined according to:

a. for one or more of a plurality of subjects:
      i. determining a Raman emission property of a portion of the tissue of the subject and acquiring biologic information concerning the subject;
      ii. determining a disease state of the subject, where "disease state" comprises the presence or likelihood of diabetes; the degree of progression of diabetes; a change in the presence, likelihood, or progression of diabetes; a probability of having, not having, developing, or not developing diabetes; the presence, absence, progression, or likelihood of complications from diabetes;
    b. applying a multivariate method to the plurality of biologic information acquisitions and Raman emission property determinations and associated disease state determinations to generate a model relating Raman emission property to disease state.

34. A method of determining disease state in an individual, where "determining a disease state" comprises determining the presence or likelihood of diabetes; the degree of progression of diabetes; a change in the presence, likelihood, or progression of diabetes; a probability of having, not having, developing, or not developing diabetes; the presence, absence, progression, or likelihood of complications from diabetes, and where "determining a disease state" does not comprise measurement of glucose concentration, the method comprising:
   a. determining a Raman emission property of a portion of the skin of the individual and biologic information concerning the individual;
   b. using a multivariate method to determine a disease state of the individual from the Raman emission property and the biologic information.

35. A method according to claim 34, wherein:
   a. the Raman emission property comprises the intrinsic Raman emission of the portion of the skin;
   b. the disease state comprises the presence of diabetes;
   c. using a multivariate method comprises applying a multivariate model relating intrinsic Raman emission of skin and biologic information to disease state.

36. A method according to claim 34, wherein determining a Raman emission property comprises determining the tissue's response to amplitude-modulated excitation light, a short pulse of excitation light, or polarized excitation light, or a combination thereof.

37. A method according to claim 34, wherein determining a Raman emission property comprises the using confocal detection or optical coherence tomography to discriminate the tissue depth from which the Raman emission property originates.

38. A method according to claim 34, wherein determining a Raman emission property comprises using raster scanning or imaging optics to obtain information regarding the spatial distribution of the Raman emission property.

39. A method as in claim 1, wherein the tissue comprises the dermis of the individual.

40. A method as in claim 21, wherein the tissue is not the eye, and wherein applying a multivariate method comprises applying a multivariate model constructed using a nonlinear technique.

* * * * *